US006692480B1

(12) United States Patent
Bush

(10) Patent No.: US 6,692,480 B1
(45) Date of Patent: Feb. 17, 2004

(54) METHOD AND APPARATUS FOR TREATING AND PREVENTING URINARY TRACT INFECTIONS

(75) Inventor: Irving M. Bush, 10N268 Switzer Ave., Elgin, IL (US) 60123

(73) Assignee: Irving M. Bush, West Dundee, IL (US)

( * ) Notice: Subject to any disclaimer, the term of this patent is extended or adjusted under 35 U.S.C. 154(b) by 0 days.

(21) Appl. No.: 09/698,645

(22) Filed: Oct. 27, 2000

(51) Int. Cl.$^7$ .............................................. A61M 31/00
(52) U.S. Cl. ........................ 604/500; 604/329; 604/402
(58) Field of Search .................................. 604/500, 315, 604/317, 544, 541, 329, 349, 346, 397, 402, 206

(56) References Cited

U.S. PATENT DOCUMENTS

| | | |
|---|---|---|
| 3,946,737 A | 3/1976 | Kobler |
| 3,986,511 A | 10/1976 | Olofsson et al. |
| 4,135,021 A | 1/1979 | Patchell et al. |
| 4,175,561 A | 11/1979 | Hirschman |
| 4,211,225 A | 7/1980 | Sibalis |
| 4,291,696 A | 9/1981 | Ring |
| 4,294,253 A | 10/1981 | Friese |
| 4,351,339 A | 9/1982 | Sneider |
| 4,533,356 A | 8/1985 | Bengmark et al. |
| 4,624,668 A | 11/1986 | Siegers |
| 4,661,101 A | 4/1987 | Sustmann |
| 4,705,514 A | 11/1987 | Barnard |
| 4,743,237 A | 5/1988 | Sweere |
| 5,374,258 A | 12/1994 | Lloyd et al. |

OTHER PUBLICATIONS

We Stamm, R. Raz "A controlled trial of intravaginal estriol in postmenopausal women with recurrent urinary tract infections", N Eng J Med 1993 Sep. 9; 329 (11): 753–6, 1.http://www.ncbi.nlm.nih.gov/entrez/query.fcgi?CMD=Text&DB=PubMed.

William D. Haggard, Jr., M.D. "Cystitis In Women", JAMA, May 28, 1997, vol. 277, No. 20, 1590.
Endre Ludwig, MD, PhD, "Bacteriuria in Women with Diabetes Mellitus", Therapeutic Challenges, Supplement Infections in Urology, S3–S6.
Irving H. Gomolin, MD, Jack D. McCue, MD, "Urinary Tract Infection in the Elderly Patient", Geriatric Outlook, Supplement Infections in Urology, S7–S13.
WebMD.com, "Urinary Tract Infection", Nidus Information Services, Inc. Well–Connected Report, Sep. 1998, 1–18, http://my.webmd.com/content/dmk/dmk_/dmk_article_ 40086.
Walter E. Stamm, MD, "Clinical approach to infections of the urinary tract", Supplement to Hospital Medicine, vol. 32 No. 6S–A, 1996, 1–24.
Anthony J. Schaeffer, M.D., "Infections of the Urinary Tract", Sixth Edition, Campbell's Urology, 1992, 731–806.
J. Curtis Nickel, MD, Robert J.C. McLean, PhD, "Bacterial Biofilms in Urology", Nov./Dec. 1998 Infections in Urology, 169–175.
Charles Bankhead, UT Contributing Editor, "Epithelial model clarifies early stages of UTIs", Urology Times, Sep. 2000.

(List continued on next page.)

Primary Examiner—Edward K. Look
Assistant Examiner—Kimya N McCoy
(74) Attorney, Agent, or Firm—Sonnenschein, Nath & Rosenthal LLP

(57) ABSTRACT

A method and apparatus for treating urinary tract infections in females is described. The method includes inserting a urine control device into a vagina of a female; followed by having the female urinate; and followed by removing the urine control device from the vagina. Preferably, the urine control device includes an anti-microbial agent. In one embodiment, the apparatus includes an absorptive device for absorbing bodily fluids, and an elongated member attached to the absorptive device for removing the absorptive device from a vagina. Preferably, the absorptive device includes an anti-microbial agent.

20 Claims, 6 Drawing Sheets

OTHER PUBLICATIONS

Lindsay E. Nicolle, M.D., "Asymptomatic Bacteriuria–Important or Not?", N Eng J Med, Oct. 5, 2000, vol. 343, No. 14, 1037–1039.

Thomas M. Hooton et al., "A Prospective Study of Asymptomatic Bacteriuria in Sexually Active Young Women", New Eng J of Med, Oct. 5, 2000, vol. 343, No. 14, 992–997.

Health Keeper Inc. "Never Buy Tampons or Pads Again, *The Keeper Menstrual Cap*", http://www.keeper.com/main.htm, Oct. 19, 2000, 1–3.

Many Moons Alternative *"How to Make your own Washable Cotton Pads"*, http://www.pacificcoast.net/~manymoons/howto.html, Oct. 19, 2000, 1–2.

Many Moons Alternative "Alternative Menstruation Products by Many Moons", http://www.pacificcoast.net/~manymoons/, Oct. 19, 2000, 1–3.

Timothy P. Bukowski, M.D., "Evaluation and Treatment of Pediatric Urinary Tract Infections", Mediguide to Urology, vol. 12, Issue 1.

METHOD AND APPARATUS FOR TREATING AND PREVENTING URINARY TRACT INFECTIONS

FIELD OF THE INVENTION

The present invention relates to a method and apparatus for treating and preventing urinary tract infections. More particularly, the present invention relates to a method and apparatus for treating and preventing urinary tract infections in females.

BACKGROUND

FIGS. 1 and 2 illustrate a urinary system 20 that helps maintain proper water and salt balance throughout a female 30. Two kidneys 22 are located on each side of the body to help filter waste products, water, and salts from the blood to form urine 36. Urine 36 passes from each kidney 22 to the bladder 26 through thin tubes referred to herein as ureters 24. Bladder 26 stores urine 36, which is then eliminated from the body via another tube called a urethra 28. One major problem that occurs within urinary system 20 is a urinary tract infection. A urinary tract infection is an infection in urinary system 20 caused by microorganisms such as bacteria, viruses, and fungi.

The human body has many defenses to urinary tract infections. For example, urine is normally sterile, that is free of bacteria, viruses, and fungi that can cause urinary tract infections. In fact, urine functions as an antiseptic, washing potentially harmful microorganisms out of the body to help prevent urinary tract infections. Additionally, ureters 24, which are used to carry urine from the kidneys 22 to the bladder 26, are designed at their distal end to prevent urine from backing up into the kidney 22. In females, the urethral gland secretes infection-fighting substances that help prevent urinary tract infections. Moreover, the immune system in a female continuously fights microorganisms.

Nevertheless, urinary tract infections are the second most common of all infections and can occur throughout the lifetime of an individual. On average, 10% to 20% of all women will develop a urinary tract infection at some time in their lives, and women are up to 30 times more likely to have urinary tract infections than men. Urinary tract infections are predominantly bacterial infections. The bacteria *Escherichia coli* is responsible for up to 85–90% of urinary tract infections. *Staphylococcus saprophyticus* is the second major bacterial culprit, causing 5% to 15% of cases in women. Other species of bacteria responsible for urinary tract infections include, Klebsiella, *Proteus mirabilis*, Pseudomanas, *Ureaplasma urealyticum*, and Enterococci. In most cases of urinary tract infections, *E. coli*, which originates as a harmless microorganism in the intestines, spreads to the vaginal passage where it invades and colonizes the urinary tract. In some cases, bacteria come from the uterus during menstruation or from unprotected sexual intercourse. In recurrent urinary tract infections, later infections are often caused by bacteria that are different from those that caused a previous or first infection; even if the later bacteria is still *E. coli*, it may be a different strain from that causing the previous infection.

The most common type of urinary tract infection is cystitis. Cystitis is an infection that occurs in the lower urinary tract, affecting the bladder and urethra and almost always occurs in women. Bacteria from fecal matter are easily transferred to the vagina and the urethra. In most cases, the infection is brief and acute and only the surface of the bladder is infected. Deeper layers of the bladder may be harmed if the infection becomes persistent, or chronic, or if the urinary tract is structurally abnormal. When infection is limited only to the urethra, the infection is known as urethritis, which is a common sexually transmitted disease in men. A urinary tract infection can also spread to the upper tract, that is, the ureters and kidneys, and is then referred to as pyelonephritis. As many as 10–20% of all women with cystitis may have pyelonephritis at the same time as cystitis.

Often, after a first episode of a urinary tract infection, a second urinary tract infection occurs a few months later. If three or more urinary tract infections occur over a two year period, the condition is referred to as a recurrent urinary tract infection. Recurrent urinary tract infections in certain women may be due to an increase in pH levels within the vagina. In normally fertile women 30, a vagina 32 is colonized by lactobacilli, microorganisms that maintain a highly acidic environment, that is, an environment with a low pH of between about 4 and about 5, that is hostile to other bacteria. In addition, lactobacilli produce hydrogen peroxide, which helps eliminate bacteria and reduces the ability of *E. coli* to adhere to vaginal cells. When there is an increase in the pH level in vagina 32, bacterial growth becomes prevalent and the risk of urinary tract infection is increased.

Vaginal wetting, the introduction of urine 36 into vagina 32, may occur in some females during urination. Since urine 36 maintains a rather high pH of between about 6 and about 7, vaginal wetting can increase the pH level in the vagina to between about 7 and 9. The increased pH level caused by vaginal wetting may encourage bacterial growth and increase the risk of urinary tract infections, including recurrent urinary tract infections. Vaginal wetting may be caused by a number of factors, such as, but not limited to, large labia, structural abnormalities in urethra 28, and swelling or scarring of tissue 34 surrounding urethra 28. Some times, recurrent urinary tract infections lead to structural abnormalities in the female urethra called fibrosis. Fibrosis is a swelling or scarring of tissue 34 surrounding vagina 32 that the causes urethra 28 to shorten and point downwards into vagina 32, as illustrated in FIG. 3. Fibrosis may be caused by other factors as well, not just recurrent urinary tract infections. Females with fibrosis have an increased chance of a urinary tract infection since there is a greater chance for urine 36 to enter vagina 32 when urethra 28 is shortened and points downwards into the vagina 32.

Symptoms arising from urinary tract infections, such as pain and bladder spasms, may be treated using drugs such as phenazopyridine, methenamine, flavoxate, or methylene. However, these drugs have side effects such as headaches, allergic reactions, upset stomachs, and may turn urine a blue or orange color, which can discolor and stain fabric. Moreover, these drugs treat only the symptoms and do not cure a urinary tract infection. For people with recurrent or severe urinary tract infections antibiotic treatments are available. Oral antibiotic or antimicrobial treatment of urinary tract infections, such as cystitis, results in about an 85% initial success rate, although the rate of recurrence remains high. Additionally, antibiotic drug combinations, such as trimethoprim/sulfamethoxazole, commonly called TMP-SMX, trimethoprin (PROLOPRIM, TRIMPEX) or sulfamethoxazole (THIOSULFIL, FORTE) used alone or with the anti-microbial nitrofurantoin (FURADANTIN, MACRODANTIN), may be used to treat urinary tract infections. Other antibiotics, in addition to the ones listed above, may also be used to treat urinary tract infections.

As with any drug, there are side effects and the antibiotic drugs only treat a single occurrence of urinary tract infection, and do not prevent recurrent urinary tract infections. The rate of recurrent urinary tract infections does not seem to be affected by even successful treatments. Furthermore, the repeated use of antibiotic drugs increases the chance of bacterial resistance in the person taking the antibiotics. Bacterial resistance to antibiotics is becoming a serious problem. About one third of the bacterial strains causing UTI have become resistant to the penicillin and sulfa drugs that were once commonly used for treatment. Resistance as high as 20% has also been found with two other commonly prescribed drugs, nitrofurantoin and nalidixic acid (NEGGRAM). As bacterial resistance to antibiotics increases, the effectiveness of antibiotic treatment is decreased. Accordingly, advances in methods and apparatuses for treating urinary tract infections, are necessary.

SUMMARY

According to a first aspect of the present invention, a method for treating and preventing urinary tract infections in females is provided. The method includes inserting an absorptive device into a vagina of a female; followed by removing the absorptive device; followed by inserting a urine control device into the vagina, followed by having the female urinate; and followed by removing the urine control device from the vagina. Preferably, the absorptive device includes an anti-microbial agent.

According to another aspect of the present invention, a method for treating urinary tract infections in females is provided. The method includes inserting a urine control device into a vagina of a female; followed by having the female urinate; and followed by removing the urine control device from the vagina. Preferably, the urine control device includes an anti-microbial agent.

According to another aspect of the present invention, an apparatus for treating urinary tract infections in females is provided. Preferably, the apparatus includes an absorptive device for absorbing bodily fluids, and an elongated member attached to the absorptive device for removing the absorptive device from a vagina. Preferably, the absorptive device includes an anti-microbial agent.

According to another aspect of the present invention, a kit for treating urinary tract infections in females is provided. The kit includes at least one urine control device for treating and preventing urinary tract infections in females, and packaging surrounding the urine control device, wherein the packaging is sealed to prevent the urine control device from becoming contaminated. Preferably, the urine control device includes an absorptive device for absorbing bodily fluids and an elongated member attached to the absorptive device for removing the absorptive device from a vagina. More preferably, the absorptive device includes an anti-microbial agent.

Figure 1:
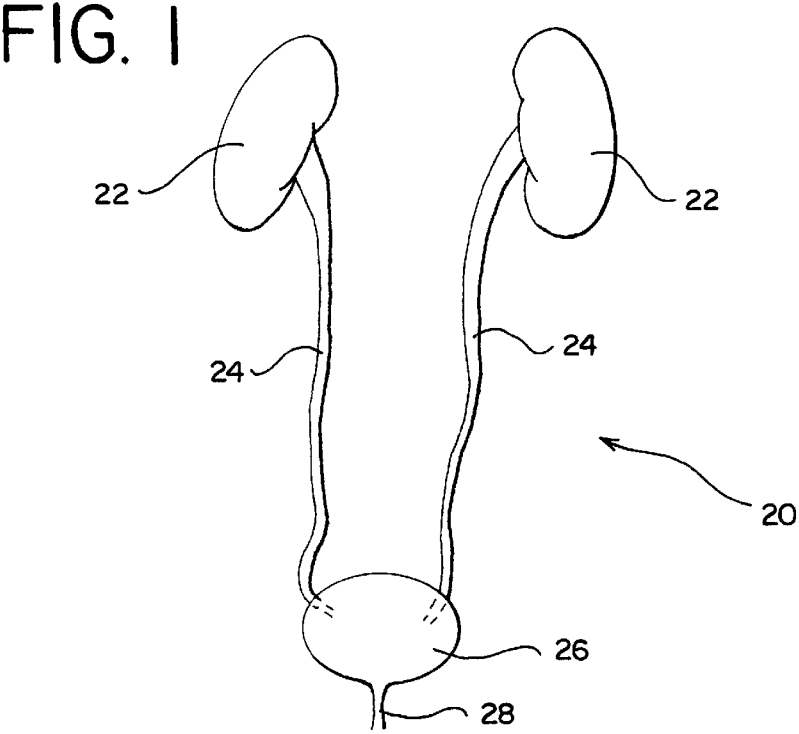
FIG. 1 is an illustrative diagram of a urinary system, in accordance with one embodiment.
Figure 2:
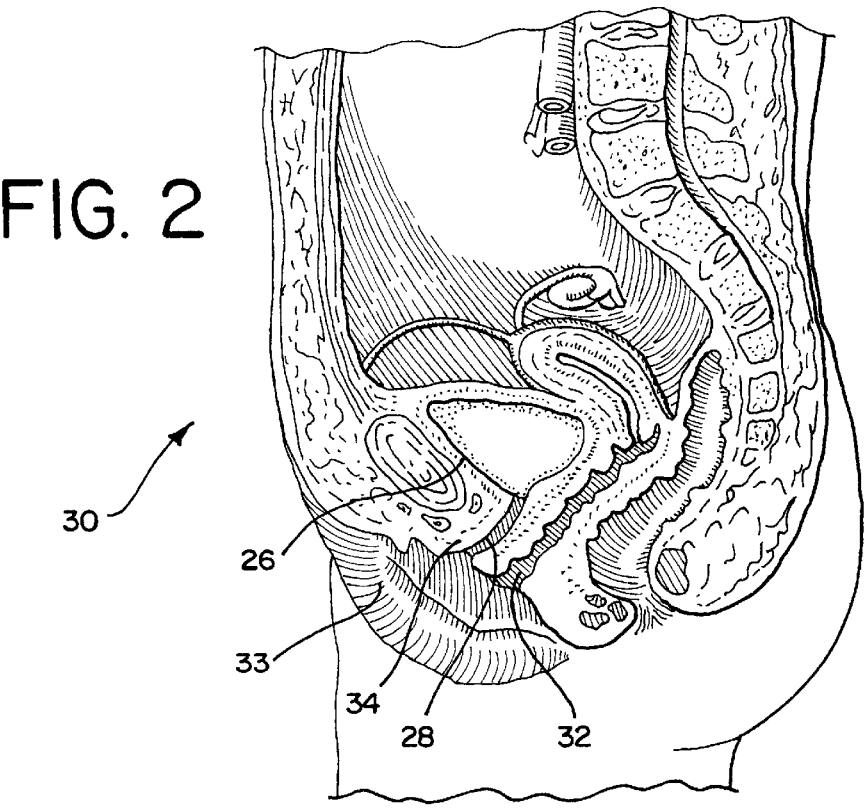
FIG. 2 is a cross-sectional side view of a portion of a female, in accordance with one embodiment.
Figure 3:
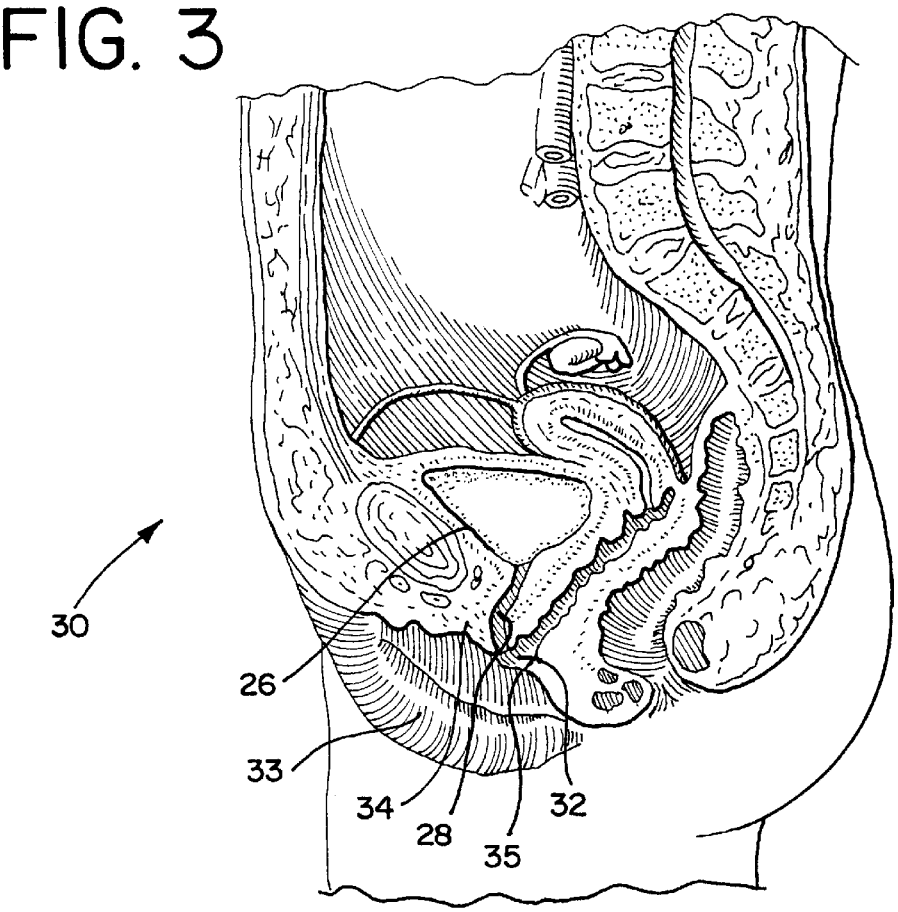
FIG. 3 is another cross sectional view of a portion of a female, in accordance with one embodiment.

For simplicity and clarity of illustration, elements shown in the Figures have not necessarily been drawn to scale. For example, the dimensions of some of the elements are exaggerated relative to each other for clarity. Further, where considered appropriate, reference numerals have been repeated among the Figures to indicate corresponding elements.

DETAILED DESCRIPTION

In order to treat and prevent urinary tract infections, the present invention employs the use of a urine control device to reduce or eliminate the amount of urine in the vagina. By reducing or eliminating the amount of urine in the vagina, the chances of bacterial growth in the vagina and a urinary tract infection in the urinary system, are reduced.

Figure 4:
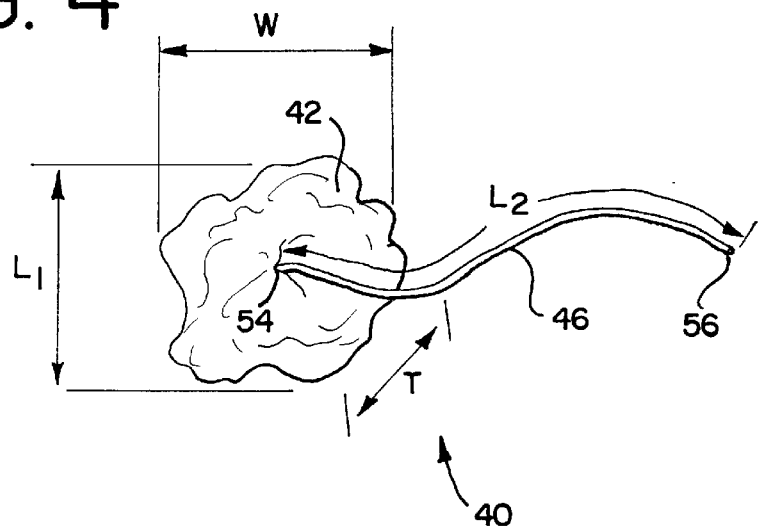
FIG. 4 is a perspective view of a urine control device, in accordance with one embodiment.

FIG. 4 illustrates one embodiment of urine control device 40 used for treating and preventing urinary tract infections in females. Urine control device 40 prevents urine 36 from entering the vagina 32 when the urine control device is inserted into vagina 32. Preferably, urine control device 40 significantly decreases or prevents urine 36 from entering into vagina 32, by either conforming the shape of urine control device 40 to the shape of vagina 32 or by conforming the shape of vagina 32 to the shape of urine control device 40. By significantly decreases, it is meant that the amount of urine 36 entering vagina 32 is reduced at least 50%, and more preferably, at least 80%. In either way, urine control device 40 blocks the vaginal introitus, or opening 35, of vagina 32 so that fluids, such as urine 36, are prevented, or significantly decreased, from entering vagina 32. Urine control device 40 can be any shape or size that can be inserted into and block the opening 35 of vagina 32. Preferably, urine control device 40 approximates the shape and size generally of vagina 32 such that upon insertion into vagina 32, urine control device 40 prevents urine from entering vagina 32.

In one embodiment, urine control device 40 includes an absorptive device 42 for absorbing fluids and for preventing fluids from entering vagina 32, as illustrated in FIG. 4. Absorptive device 42 is any device that can be used for absorbing fluids, such as, for example, bodily fluids. Bodily fluids include such things as urine 36, vaginal fluids 37, blood, water, mucous, or any other type of fluid present within a female 30. As used herein, vaginal fluids 37 refers to any fluid found within a vagina, such as urine 36, vaginal mucus, cervical mucus, and blood present in the vagina 32.

In one embodiment, a test was conducted to determine how much fluid absorptive device 42 is capable of absorbing. The test requiring filling a 5 ml graduated cylinder with water, measuring the amount of water in the 5 ml graduated cylinder, placing the absorptive device 42 fully within the 5 ml graduated cylinder until the absorptive device 42 was submersed with water, waiting a period of between fifteen and thirty seconds, and then removing the absorptive device 42. As a result of this test, it was determined that, in one embodiment, absorptive device 42 could absorb no more than about 2.1 ml of fluid. In one embodiment, absorptive device 42 is capable of absorbing no more than about 10 ml of fluid. Preferably absorptive device 42 can absorb no more than about 5 ml of fluid, and more preferably no more than about 2.5 ml of fluid.

Preferably, absorptive device 42 includes an absorptive material such as natural fibers, synthetic fibers, a natural sponge, and a synthetic sponge. Natural fibers include materials such as cotton, wool, linen, and silk. Synthetic fibers include materials such as polyester, rayon, and nylon. Absorptive device 42 has three dimensions, that is, absorptive device 42 has a width W, a length $L_1$, and a thickness T, as illustrated in FIG. 4. Preferably, the width W, the length $L_1$ and the thickness T of absorptive device 42 are all less than 4 cm. In one preferred embodiment, the width W of absorptive device 42 is between about 2 cm and about 4 cm, the length $L_1$ of absorptive device 42 is between about 2 cm and about 4 cm, and the thickness T of absorptive device 42 is between about ½ cm and about 2 cm. In one embodiment, the shape of absorptive device 42 is spherical and the width W, the length L, and the thickness T of absorptive device 42 are all between about 1 cm and about 4 cm. Absorptive device 42 may have additional shapes, such as elliptical, cylindrical, conical, frustoconical, pyramidal, frustopyramidal, box-shaped, parallelogram shaped, any shape that can conform to the contours of vagina 32, and any shape that can block entry to vagina 32.

Figure 12:
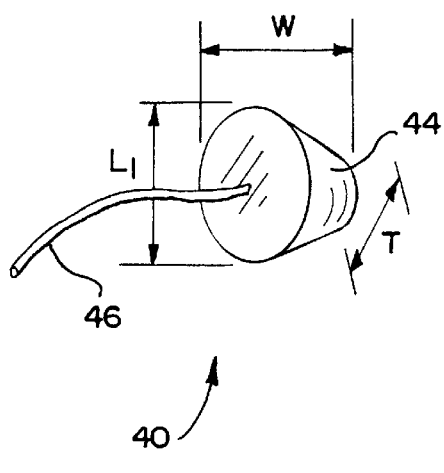
FIG. 12 is a perspective view of a urine control device, in accordance with one embodiment.
Figure 13:
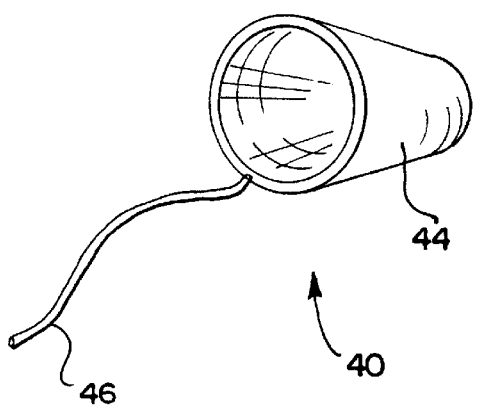
FIG. 13 is a perspective view of a urine control device, in accordance with one embodiment.

In one embodiment, urine control device 40 includes a non-absorptive device 44 for preventing fluids from entering vagina 32, as illustrated in FIGS. 12 and 13. Non-absorptive device 44 is any device that can be used for preventing fluids from entering vagina 32, such as, for example, bodily fluids. Preferably, non-absorptive device 44 includes a non-absorptive material such as rubber, plastic, latex, and silicone. Non-absorptive device 44 prevents fluids from entering vagina 32 by either conforming to the shape of vagina 32 or by conforming the shape of vagina 32 to the shape of non-absorptive device 44. In either way, non-absorptive device 44 blocks opening 35 of vagina 32 so that fluids are prevented from entering vagina 32. Non-absorptive device 44 can be any shape or size that can be inserted into and block the opening 35 of vagina 32. Preferably, non-absorptive device 44 approximates the shape and size generally of vagina 32 such that upon insertion into vagina 32, non-absorptive device 44 prevents urine from entering vagina 32. Non-absorptive device 44 has three dimensions, that is, non-absorptive device 42 has a width W, a length $L_1$, and a thickness T, as illustrated in FIG. 12. Preferably, the width W, the length $L_1$ and the thickness T of non-absorptive device 44 are all less than 4 cm. In one preferred embodiment, the width W of non-absorptive device 44 is between about 2 cm and about 4 cm, the length $L_1$ of non-absorptive device 44 is between about 2 cm and about 4 cm, and the thickness T of non-absorptive device 44 is between about ½ cm and about 2 cm. In one embodiment, the shape of non-absorptive device 44 is spherical and the width W, the length L, and the thickness T of non-absorptive device 44 are all between about 1 cm and about 4 cm. Non-absorptive device 44 may have additional shapes, such as elliptical, cylindrical, conical, frustoconical, pyramidal, frustopyramidal, box-shaped, parallelogram shaped, any shape that can conform to the contours of vagina 32, and any shape that can block entry to vagina 32. In one embodiment, non-absorptive device 44 is hollow, and has a cup-shape, as illustrated in FIG. 13. In another embodiment, non-absorptive device 44 is solid, as illustrated in FIG. 12.

In one embodiment, urine control device 40 includes an elongated member 46 for removing the urine control device 40 from vagina 32. Preferably, elongated member is attached to absorptive device 42 or non-absorptive device 44, as illustrated in FIGS. 4, 12, and 13. Elongated member 54 has a first end 54 attached to absorptive device 42 or non-absorptive device 44, and a second end 56 opposed to first end 54. Elongated member 46 assists in removing urine control device 40 from vagina 32. Elongated member 46 has a length $L_2$ defined as the developed length from first end 54 to second end 56. Preferably, elongated member 46 has a length L2 that is between about 3 cm and about 20 cm, and more preferably between about 6 cm and about 14 cm. Preferably, elongated member 46 is a long, flexible member such as a string, a wire, and a tab, such as a plastic tab. Elongated member 46 is attached to absorptive device 42 or non-absorptive device 44 using any method known to one of ordinary skill in the art for attaching a first member to a second member, such as, gluing, welding, stapling, forming a knot, stitching, and interweaving elongated member with absorptive device 42 or non-absorptive device 44. In one embodiment, elongated member 46 is attached to absorptive device 42 or non-absorptive device 44 by sewing elongated member 46 to absorptive device 42 or non-absorptive device 44. Preferably, a tacker machine, such as the CHANDLER TACK MASTER Model 555-75 from Chandler machine of Baldwin, N.Y., is used to sew elongated member 46 to absorptive device 42 or non-absorptive device 44.

In one embodiment, urine control device 40 includes an anti-microbial agent 48, as illustrated in FIGS. 5–9. Antimicrobial agent 48 is any agent which can kill or destroy microbes such as viruses, fungi, and bacteria. Preferably, antimicrobial agent 48 is an agent such as NEOSPORINT™, BETADINE, alcohol, penicillin, BACTROBAN, GEUTAMYCIN, and antifungal agents such as LOTRISONE or 70% aloe.

Figure 10:
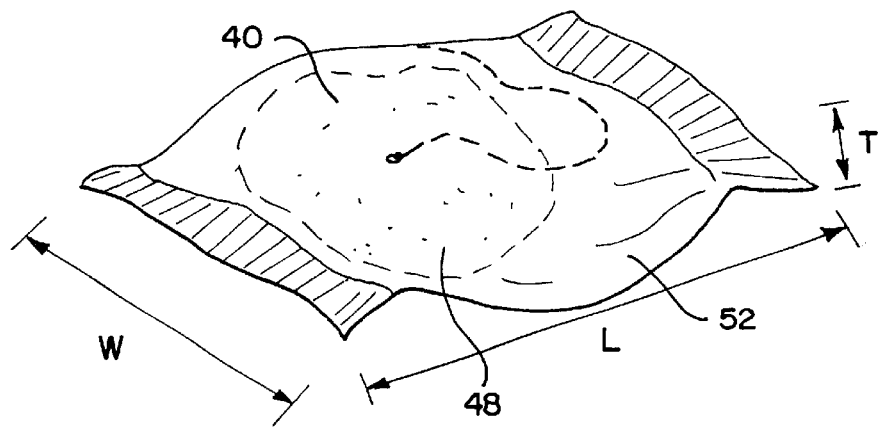
FIG. 10 is a perspective view of a urine control device sealed within a packaging unit, in accordance with one embodiment.

In one embodiment, urine control device 40 is surrounded by packaging 52, as illustrated in FIG. 10. Preferably, packaging is less than 10cm in width W, length L, and thickness T, as illustrated in FIG. 10. Preferably, urine control device 40 is sealed within packaging 52 to prevent urine control device 40 from contamination. More preferably, urine control device 40 is hermetically sealed within packaging 52 to prevent urine control device 40 from contamination. In one embodiment, urine control device 40 is sterilized before being sealed within packaging 52. Urine control device can be sterilized by a number of methods known to those skilled in the art, such as autoclaving, or using ethylene oxide gas. Preferably, packaging 40 includes a material such as plastic, paper, metallic foil, and reinforced cardboard. In one embodiment, at least two urine control devices 40 are surrounded by a single packaging 52.

Figure 11:
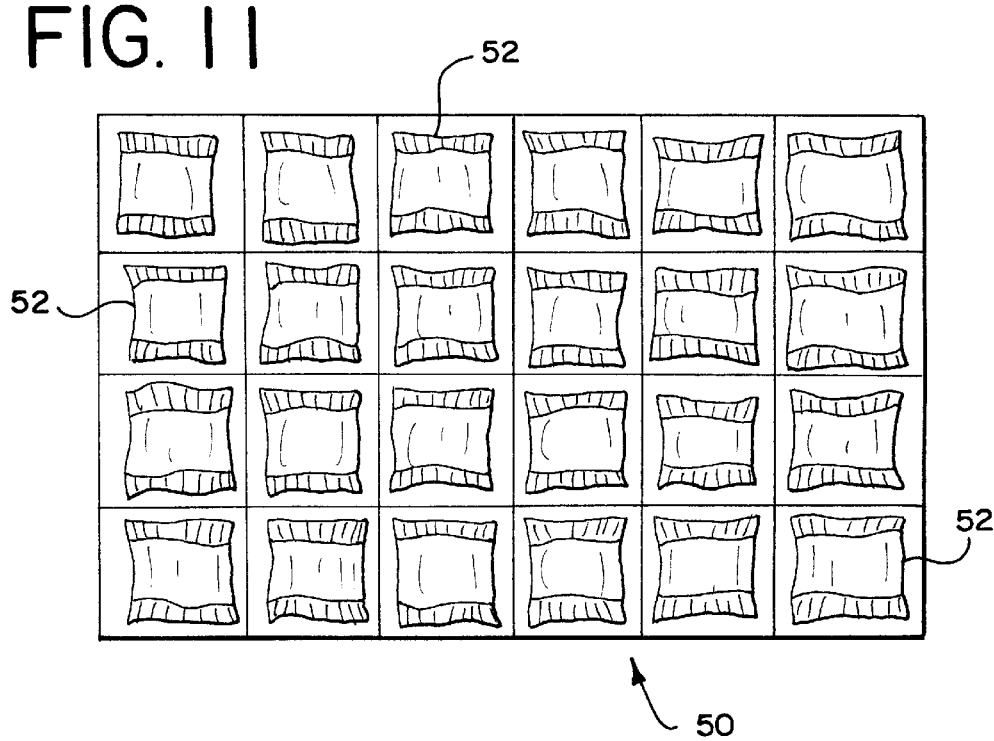
FIG. 11 is an overhead view of a kit for treating and preventing urinary tract infections, in accordance with one embodiment.

In one embodiment, a kit 50 for treating urinary tract infections in females 30 is provided, as illustrated in FIG. 11. Kit 50 includes at least one urine control device 40 for treating and preventing urinary tract infections. Preferably, kit 50 includes between 2 and 70 urine control devices 40, and more preferably, kit 50 includes about 24 urine control devices 40, as illustrated in FIG. 11. In one embodiment, kit 50 includes an anti-microbial agent 48 that can be applied to urine control device 40. In one embodiment, kit 50 includes an antibiotic lubricant, such as BETADINE, BACTROBAN, and GEUTAMYCIN, to ease the insertion of urine control device 40 into vagina 32. In one embodiment, kit 50 includes packaging 52 surrounding urine control device 40, wherein the packaging 52 is sealed to prevent the urine control device 40 from becoming contaminated.

Figure 7:
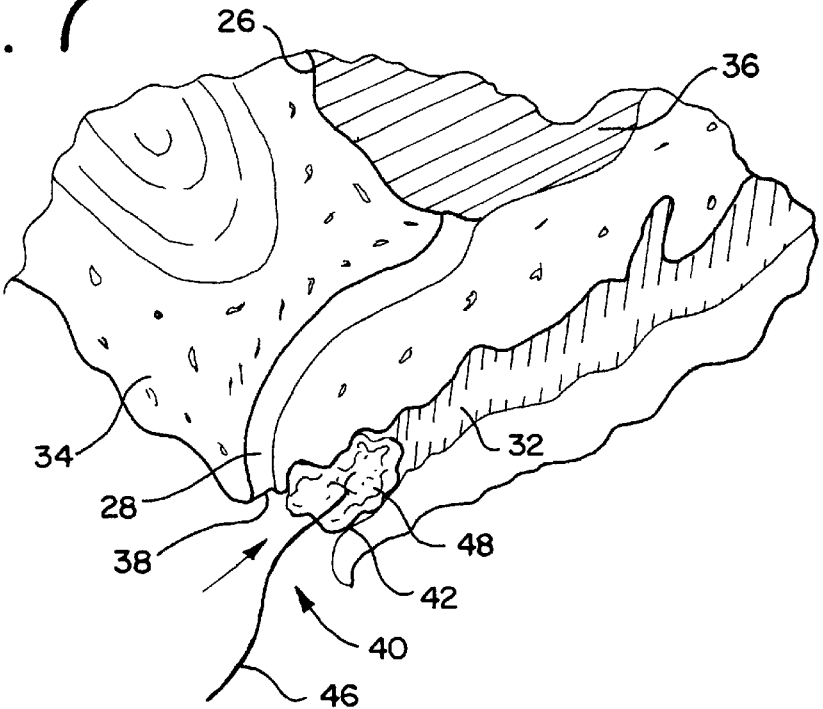
Figure 8:
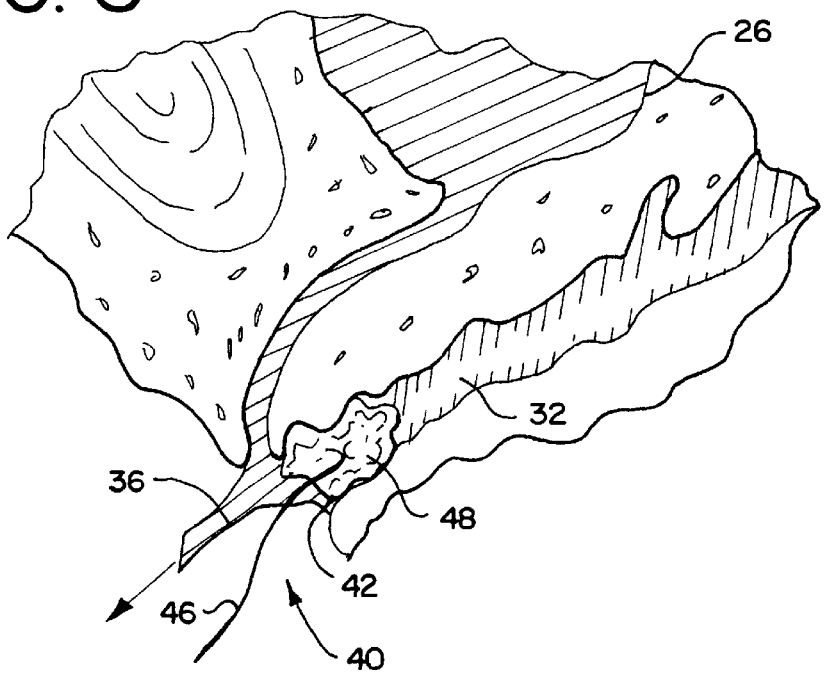
Figure 9:
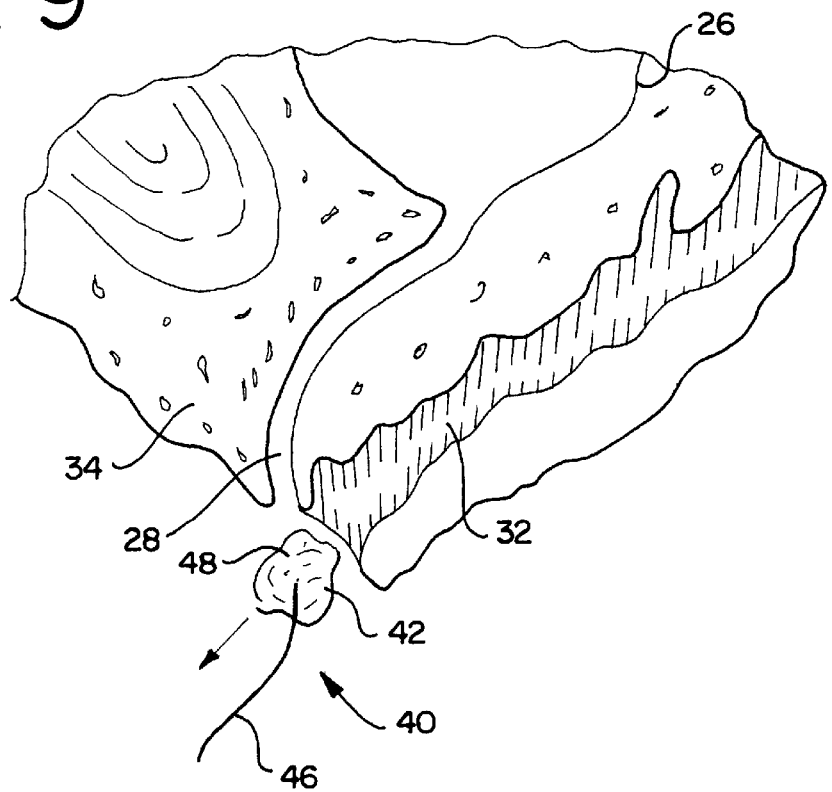

In one embodiment, a method for treating and preventing urinary tract infections in females is provided, as illustrated in FIGS. 7–9. The method includes inserting a urine control device 40 into a vagina 32 to prevent urine from entering vagina 32, as illustrated in FIG. 7. Preferably, the inserting of the urine control device 40 is just beyond the opening 38 of urethra 28, as illustrated in FIG. 7. The inserting of the urine control device 40 is followed by having the female urinate, that is, having female remove urine from bladder 26, as illustrated in FIG. 8. The having of the female urinate is followed by removing of urine control device 40 from vagina 32, as illustrated in FIG. 9. Preferably, the removing of the urine control device 40 occurs within five minutes of the having of the female urinate. More preferably, the removing of the urine control device 40 occurs within fifteen seconds of the having of the female urinate. Preferably, the urine control device 40 is attached to an elongated member 46. More preferably, a portion of the elongated member 46 is outside of the vagina 32 after the inserting of the urinary control device 40. In one embodiment, the inserting of the urine control device 40 and the removing of the urine control device 40 is repeated for at least more than 50% of the time the female urinates during a period of between about one and six months.

Figure 5:
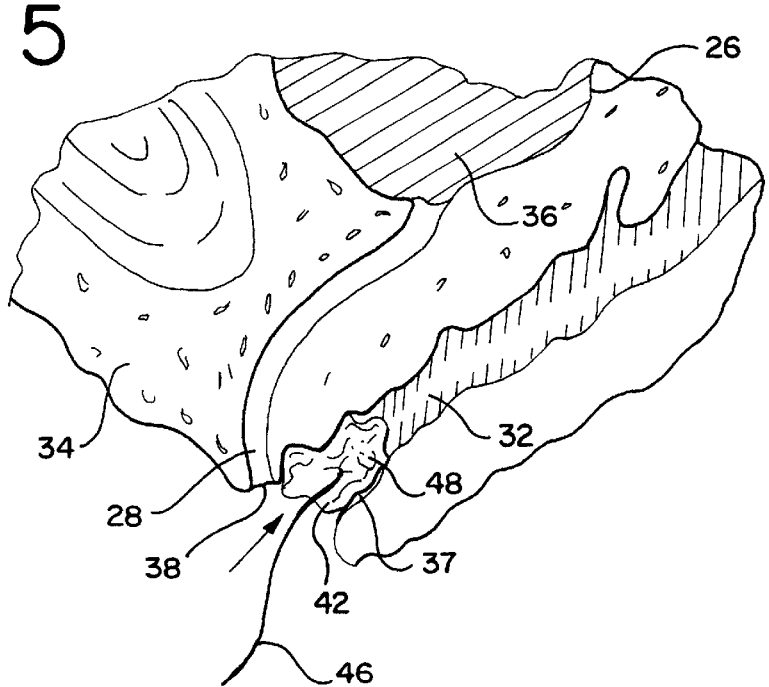
FIGS. 5–9 illustrate a method for treating and preventing urinary tract infections, in accordance with one embodiment.
Figure 6:
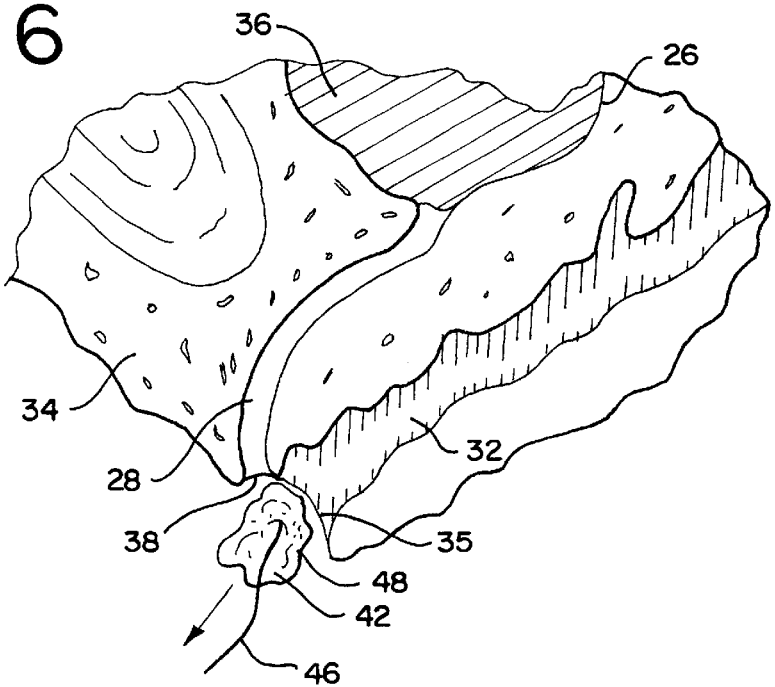

In one embodiment, a method for treating and preventing urinary tract infections in females, is provided, as illustrated in FIGS. 5–9. The method includes inserting an absorptive device 42 into a vagina 32, as illustrated in FIG. 5. Preferably, the inserting of the absorptive device 42 is just beyond the opening 38 of urethra 28, as illustrated in FIG. 5. The inserting of the absorptive device 42 is done to soak up any fluids or material that reside in the area of vagina 32 which is near opening 38 of urethra 28. The inserting of the absorptive device 42 is followed by removing the absorptive device 42, as illustrated in FIG. 6. Preferably, the removing of the absorptive device 42 occurs within five minutes of the inserting of the absorptive device 42. The removing of the absorptive device 42 is followed by inserting a urine control device 40 into the vagina to prevent urine from entering vagina 32, as illustrated in FIG. 7. Preferably, the inserting of the urine control device 40 is just beyond the opening 38 of urethra 28, as illustrated in FIG. 7. Preferably, the inserting of the urine control device 40 occurs within five minutes of the removing of the absorptive device 42.

The inserting of a urine control device 40 is followed by having the female urinate, that is, having the female remove urine from bladder 26, as illustrated in FIG. 8. The having of the female urinate is followed by removing of urine control device 40 from vagina 32, as illustrated in FIG. 9. Preferably, the removing of the urine control device 40 occurs within five minutes of the having of the female urinate. Preferably, the absorptive device 42 and/or the urine control device 40 are each attached to an elongated member 46. More preferably, a portion of the elongated member 46 is outside of the vagina 32 after the inserting of the absorptive device 42 and/or the urinary control device 40. More preferably, the portion of the elongated member 46 outside of the vagina 32 after the inserting of the absorptive device 42 and/or the urinary control device 40 is between 3 cm and 12 cm in length $L_2$. In one embodiment, the inserting of the urine control device 40 and the removing of the urine control device 40 is repeated for at least more than 50% of the time the female urinates during a period of between about one and six months.

In one embodiment, a method for treating and preventing urinary tract infections in females 30, is provided. The method includes having a female assume a squatting position. Upon assuming a squatting position, the method then requires spreading the labia 33 apart. By assuming a squatting position and spreading the labia 33 apart, the amount of splatter causes by the urine 36 exiting the urethra 28 is reduced, and therefore the amount of urine 36 entering vagina 32 can be reduced. The spreading of the labia 33 apart is followed by having the female urinate. Preferably, the having of the female urinate occurs concurrently with the spreading of the labia 33 apart. Preferably, the method also includes the taking of an anti-microbial agent 48 orally before having the female assume a squatting position. More preferably, the anti-microbial agent 48 is taken orally at least once per day. In one embodiment, in anticipation of sexual intercourse, the having of the female urinate is followed by having the female drink between about 16 and about 48 ounces of water. The having of the female drink is followed by the female engaging in sexual intercourse. Upon performing sexual intercourse, the female then urinates a second time. This method can be used either alone or in conjunction with any of the above-described methods.

Thus, there has been disclosed in accordance with the invention, a method and apparatus for treating urinary tract infections in females using a urine control device that fully provides the advantages set forth above. Although the invention has been described and illustrated with reference to specific illustrative embodiments thereof, it is not intended that the invention be limited to those illustrative embodiments. Those skilled in the art will recognize that variations and modifications can be made without departing from the spirit of the invention. It is therefore intended to include within the invention all such variations and modifications that fall within the scope of the appended claims and equivalents thereof.

What is claimed is:

1. A method for treating and preventing urinary tract infections in females, comprising:
    (a) inserting an absorptive device into a vagina of a female; followed by
    (b) removing the absorptive device; followed by
    (c) inserting a urine control device into the vagina; followed by
    (d) having the female urinate; followed by
    (e) removing the urine control device from the vagina.

2. The method of claim 1, wherein the urine control device comprises an absorptive device.

3. The method of claim 1, wherein the absorptive device comprises a material selected from the group consisting of natural fibers, synthetic fibers, a natural sponge, and a synthetic sponge.

4. The method of claim 1, wherein the absorptive device comprises an anti-microbial agent.

5. The method of claim 1, wherein the absorptive device is attached to an elongated member.

6. The method of claim 1, further comprising repeating the inserting of the urine control device and the removing of the urine control device for at least 50% of the time the female urinates during a period of between about one and six months.

7. The method of claim 6, wherein the removing of the absorptive device occurs within five minutes of the inserting of the absorptive device.

8. The method of claim 1, wherein the removing of the urine control device occurs within five minutes of having the female urinate.

9. The method of claim 8, wherein the inserting of the urine control device occurs within five minutes of the removing of the absorptive device.

10. A method for treating urinary tract infections in females, comprising:

(a) inserting a urine control device into a vagina of a female; followed by (b) having the female urinate; followed by (c) removing the urine control device from the vagina, wherein the urine control device comprises an absorptive device, and wherein the absorptive device includes an anti-microbial agent.

11. A method for treating urinary tract infections in females, comprising:

(a) inserting a urine control device into a vagina of a female; followed by (b) having the female urinate, followed by (c) removing the urine control device from the vagina, wherein the urine control device comprises an absorptive device attached to the elongated member, and wherein the elongated member is sewn through the absorptive member.

12. An apparatus for treating urinary tract infections in females, the apparatus comprising:

an absorptive device for absorbing bodily fluids, wherein the absorptive device absorbs no more than 5 ml of fluid; and an elongated member attached to the absorptive device for removing the absorptive device from a vagina.

13. The device of claim 12, wherein the absorptive device includes an anti-microbial agent.

14. The device of claim 12, wherein the absorptive device absorbs no more than about 2.5 ml of fluid.

15. The device of claim 12, wherein the elongated member is sewn into the absorptive device using a tacker machine.

16. A kit for treating urinary tract infections in females, the kit comprising:

at least one urine control device comprising an absorptive device and an elongated member attached to the absorptive device, wherein the absorptive device absorbs no more than 5 ml of fluid; and packaging surrounding the urine control device, wherein the packaging is sealed to prevent the urine control device from becoming contaminated.

17. The kit of claim 16, wherein the packaging comprises a material selected from the group comprising plastic, metallic plastic, metallic foil, and paper.

18. The kit of claim 16, wherein the absorptive device comprises an anti-microbial agent.

19. The kit of claim 16, wherein the absorptive device absorbs no more than 2.5 ml of fluid.

20. The kit of claim 16, wherein the elongated member is sewn into the absorptive device using a tacker machine.

* * * * *